(12) United States Patent
Goff et al.

(10) Patent No.: US 6,931,899 B2
(45) Date of Patent: Aug. 23, 2005

(54) SWAGING TECHNOLOGY

(75) Inventors: Edward Goff, Phoenix, AZ (US); Tom Motsenbocker, Flagstaff, AZ (US)

(73) Assignee: Machine Solutions, Inc., Flagstaff, AZ (US)

( * ) Notice: Subject to any disclaimer, the term of this patent is extended or adjusted under 35 U.S.C. 154(b) by 0 days.

(21) Appl. No.: 10/643,719

(22) Filed: Aug. 18, 2003

(65) Prior Publication Data

US 2004/0096538 A1 May 20, 2004

Related U.S. Application Data

(60) Provisional application No. 60/404,074, filed on Aug. 16, 2002.

(51) Int. Cl.[7] .............................................. B21D 39/04
(52) U.S. Cl. ......................... 72/18.1; 72/402; 29/283.5
(58) Field of Search ........................... 72/402, 76, 408, 72/16.2, 17.3, 18.2, 19.5, 18.1; 29/237, 282, 283.5

(56) References Cited

U.S. PATENT DOCUMENTS

| | | | | | |
|---|---|---|---|---|---|
| 2,114,171 A | * | 4/1938 | Benbow | ........................ | 72/76 |
| 2,114,302 A | * | 4/1938 | Harter | ........................ | 72/364 |
| 2,410,742 A | * | 11/1946 | Newall | ........................ | 72/21.2 |
| 3,177,695 A | * | 4/1965 | Van Oort | ..................... | 72/402 |
| 4,567,650 A | * | 2/1986 | Balyasny et al. | ............. | 29/822 |
| 4,578,983 A | * | 4/1986 | Kimura | ....................... | 72/407 |
| 4,644,777 A | * | 2/1987 | Kumeth | ....................... | 72/402 |
| 5,411,521 A | * | 5/1995 | Putnam et al. | .............. | 606/225 |
| 5,951,540 A | * | 9/1999 | Verbeek | ........................ | 606/1 |
| 6,360,577 B2 | * | 3/2002 | Austin | ......................... | 72/402 |
| 6,510,722 B1 | * | 1/2003 | Ching et al. | .................. | 72/402 |
| 6,568,235 B1 | * | 5/2003 | Kokish | ........................ | 72/402 |

* cited by examiner

Primary Examiner—Daniel C. Crane
(74) Attorney, Agent, or Firm—Skinner and Associates

(57) ABSTRACT

A swager for swaging marker bands to a medical catheter, comprises an article input mechanism, the article input mechanism having a first input roller assembly for receiving and conveying an article, a first sensor for detecting a predetermined aspect of the article, a second input roller assembly for receiving and conveying the article, a positioning roller assembly for precisely aligning the article with respect to the swaging head, and a second sensor all constructed and arranged in a streamwise orientation. The swager also has a radial compression swaging head with a central swaging aperture, the swaging head being aligned and communicatively coupled with the input mechanism to receive an input article from the article input mechanism and to swage the article, the swaging head being rotatable and including (i.) a unitary die plate including a plurality of die segments movably coupled to each other to provide a radial compressive force to the article disposed in the central swaging aperture; and (ii.) a closing plate pivotally coupled with respect to each other. The swager also has an output mechanism aligned and communicatively coupled with the swaging head to receive the swaged article. A swaging head and die are also disclosed.

17 Claims, 17 Drawing Sheets

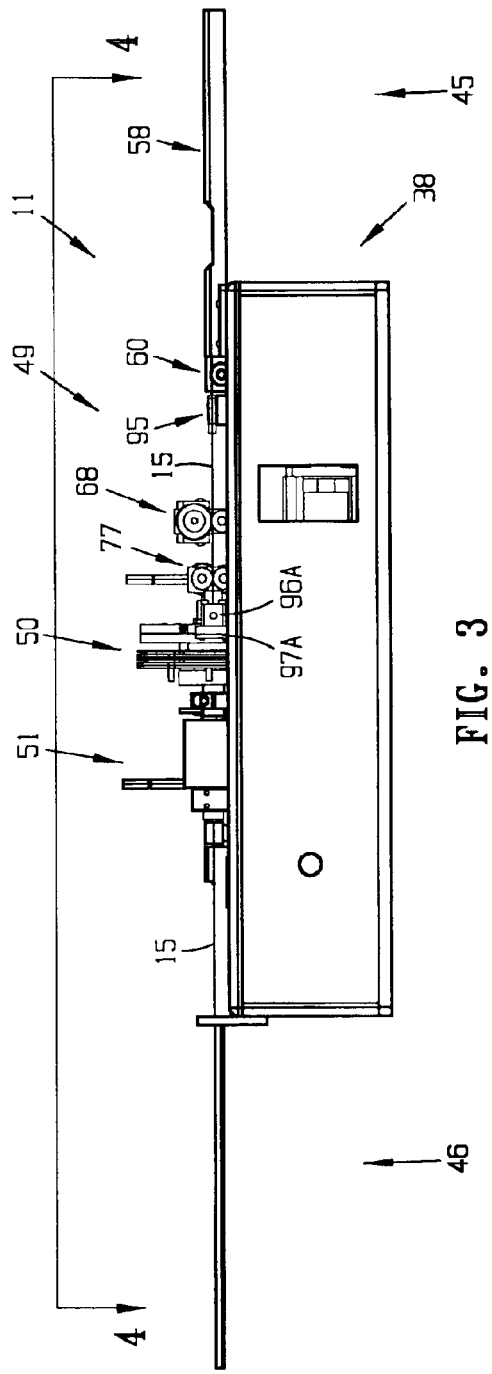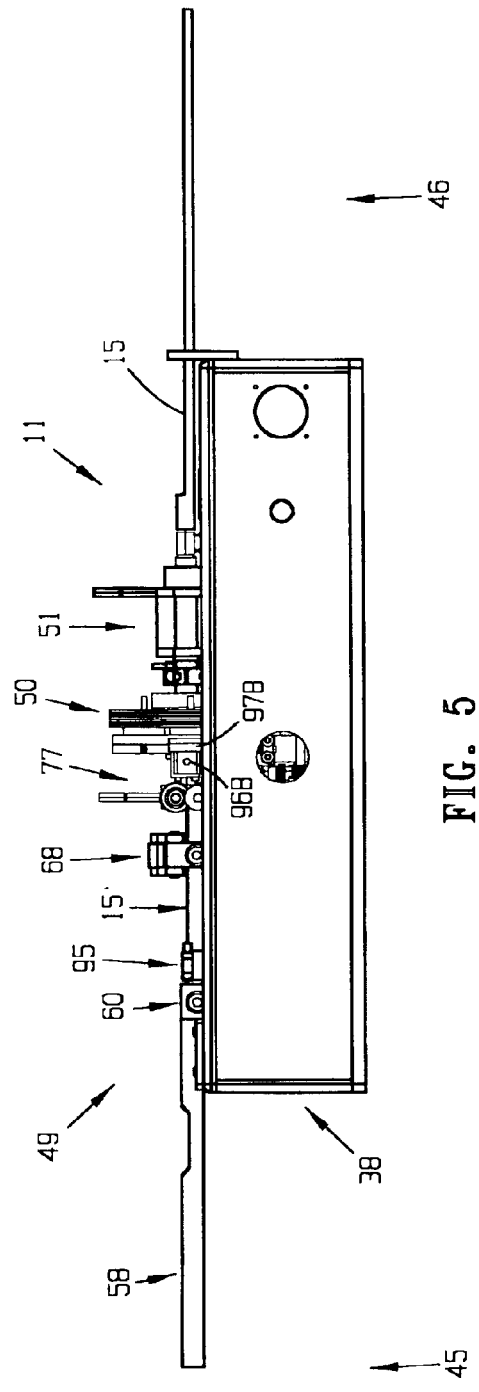

SWAGING TECHNOLOGY

CROSS-REFERENCE TO RELATED APPLICATIONS, IF ANY

This application claims the benefit of provisional application No. 60/404,074, filed Aug. 16, 2002.

37 C.F.R. §1.71(e) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX. IF ANY

Not applicable.

BACKGROUND

1. Field

The present invention relates, generally, to material forming systems, apparatus and processes. More particularly, the invention relates to a swaging system, apparatus and method. Most particularly, the invention relates to a system, apparatus and method for swaging one or more articles such as marker bands at precise locations on a tubular structure such as a medical catheter. The techniques of the invention can also be used in other fields such as tube joining, cable joining, sealing, bullet manufacturing, and other medical, industrial, commercial apparatus and processes.

2. Background Information

Swaging is a forming process for use with hollow or solid material or articles, particularly metallic material or articles. Examples of hollow material or articles include tubes, casings, catheters, needles and the like. Examples of solid materials include rods, bars and wires. Swaging is commonly used to reduce or increase the diameter of material or articles, to create particular geometric shapes or profiles of material or articles, to join or fasten material or articles, or to seal or finish material or articles. Swaging is typically accomplished by placing material or articles, most commonly tubes, rods, bars or wires, inside a die that applies compressive force. Typically, the force is applied by radially hammering. The radial hammering may be accompanied by rotating the die or the workpiece. Additionally, a mandrel may be placed inside articles such as tubes during compression. The inner and outer diameters of the material or articles may be of the same or differing shapes. Swaging is typically conducted cold, or at room temperature, but may be conducted hot. Swaging may be accomplished by a rotary process, a stationary spindle process, or a die closing process. Other known forming processes include crimping and pointing.

Examples of existing swaging technology includes a rotary swager provided by Torrington Swaging and Vaill End Forming Machinery. Inc. of Waterbury, Conn. The rotary swager has a motorized spindle which is slotted, in order to hold backers and the dies. The spindle passes the backers over the rollers to deliver a blow to the dies. In this rotary swaging process, a swaging head is fixed. The dies close over a work piece and form the material. When the backers are in-between two roll positions, the centrifugal forces will move them apart, making it possible for the die to open, while the dies are rotating around the workpiece. The operation continues several times and the result is a reduced round cross section of tube, bar or wire.

A stationary spindle swager, also provided by Torrington Swager has a spindle and dies which are fixed. They do not rotate around the workpiece. Instead, the head rotates. This type of machine is used to obtain cross-sectioned shapes other than round, such as triangular, square, polygonal.

A die closing swage, further provided by Torrington Swager has dies which are moved radially by a die closing device and by backers while the operation is being performed. A spindle is motorized and rotating. This type of machine is used to obtain grooves or recesses for short step transition angles or for assembly of large parts on cables or rods without having to remove the dies between operations.

Numerous medical devices exist for accessing and working within the vasculature and other internal systems of humans and other animals for minimally invasive diagnostic and therapeutic purposes. Examples of such devices include introducers, guidewires, catheters, and stents. They are typically thin, elongated structures which are inserted into arteries, veins, or body cavities through small punctures in the skin. After initial insertion, the insertable medical devices, and in particular certain portions or aspects of the devices such as balloons, blades, tips, drug delivery systems, are guided to desired locations in the body, such as the heart or other organs, by radioscopic or flouroscopic visualization. In such visualization processes, a medical practitioner views the medical device or a portion thereof in the body through a screen or other monitoring device. Visualization is enhanced or even made possible by a radiopaque marker, typically a band or series of bands of a predetermined geometry and disposed at a predetermined position(s) on the insertable medical device or portion thereof. Marker bands have been placed on insertable medical devices by existing swaging devices and processes.

Existing technology is believed to have limitations and shortcomings. For these and other reasons, a need exists for the present invention.

All US patents and patent applications, and all other published documents mentioned anywhere in this application are hereby incorporated by reference in their entirety.

BRIEF SUMMARY

The present invention provides a swaging system, apparatus and method which are practical, reliable, accurate and efficient, and which are believed to fulfil a need and to constitute an improvement over the background technology.

The swaging system, apparatus and process is useful for swaging metal bands to polymeric tubular structures in a precise, substantially automated fashion. In particular, the swaging system, apparatus and process is beneficial for swaging marker bands to medical catheters, guidewires, stents and the like. In general however, the swaging system, apparatus and process may be used for forming or processing hollow or solid material or articles, particularly those constructed of malleable metals, such as tubes, casings, catheters, needles, rods, bars and wires, to reduce or increase the diameter, to create particular geometric shapes or profiles, to join or fasten, or to seal or finish such material or articles.

In one embodiment, the invention provides a swager for swaging marker bands to a medical catheter, comprising:

a. an article input mechanism, the article input mechanism having a first input roller assembly for receiving and conveying an article, a first sensor for detecting a predetermined aspect of the article, a second input roller assembly for receiving and conveying the article, a positioning roller assembly for precisely aligning the article with respect to the swaging head, and a second sensor all constructed and arranged in a streamwise orientation;

b. a radial compression swaging head with a central swaging aperture, the swaging head being aligned and communicatively coupled with the input mechanism to receive an input article from the article input mechanism and to swage the article, the swaging head being rotatable and including:

i. a unitary die plate including a plurality of die segments movably coupled to each other to provide a radial compressive force to the article disposed in the central swaging, aperture; and ii. closing plate pivotally coupled with respect to each other; and c. an output mechanism aligned and communicatively coupled with the swaging head to receive the swaged article.

In another aspect, the invention provides a swaging apparatus for swaging a marker band to a medical catheter, comprising:

a. a unitary die plate including:

1. at least three die segments movably coupled to each other and defining a central swaging aperture, the segments being constructed and arranged to provide radial compressive force to an article disposed in the central swaging aperture, the die plate further comprising 2. a circumferential base, the segments being centrally arranged with respect to the base and connected thereto, wherein each segment:

i. is connected to the base by a radial flexure constructed as a beam and having a central beam axis aligned with the central swaging aperture:

ii. has a circumferential flexure constructed of a beam extending from a neighboring segment, the circumferential flexure being constructed and arranged to couple movement with two neighboring segments, and iii. has a pivot point, whereby application of a force on the segment causes the segment to pivot about the pivot point and apply a radial compressive force to article disposed in the central swaging aperture; and b. a closing plate pivotally coupled via the pivot points, and wherein the apparatus is rotatable.

The features, advantages, benefits and objects of the invention will become clear to those skilled in the art by reference to the following description, claims and drawings.

BRIEF DESCRIPTION OF THE SEVERAL VIEWS OF THE DRAWING

FIG. 3 is a front or elevation view of the base unit.

FIG. 5 is a rear view of the base unit.

DETAILED DESCRIPTION

Figure 1:
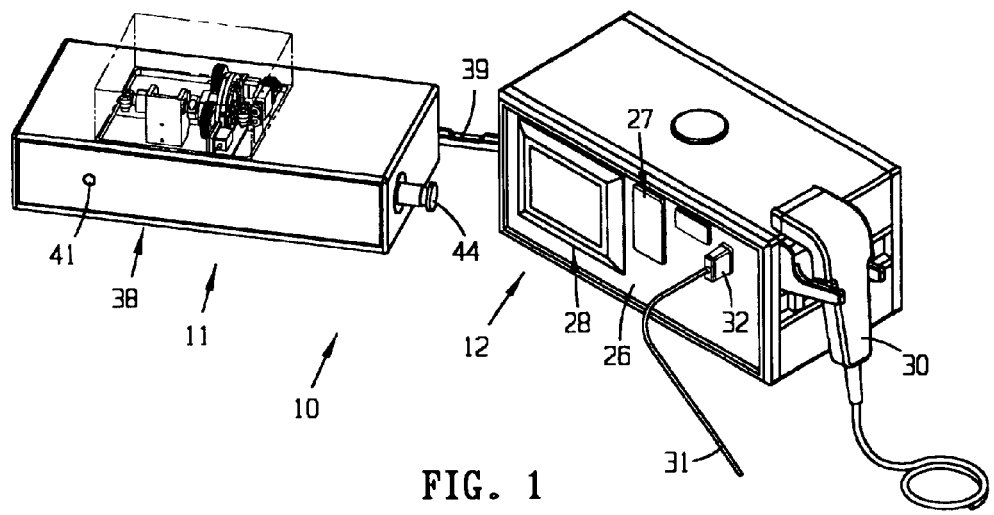
FIG. 1 is a perspective view of an embodiment of the swaging system of the present invention, showing a swaging base unit and a control unit.
Figure 2:
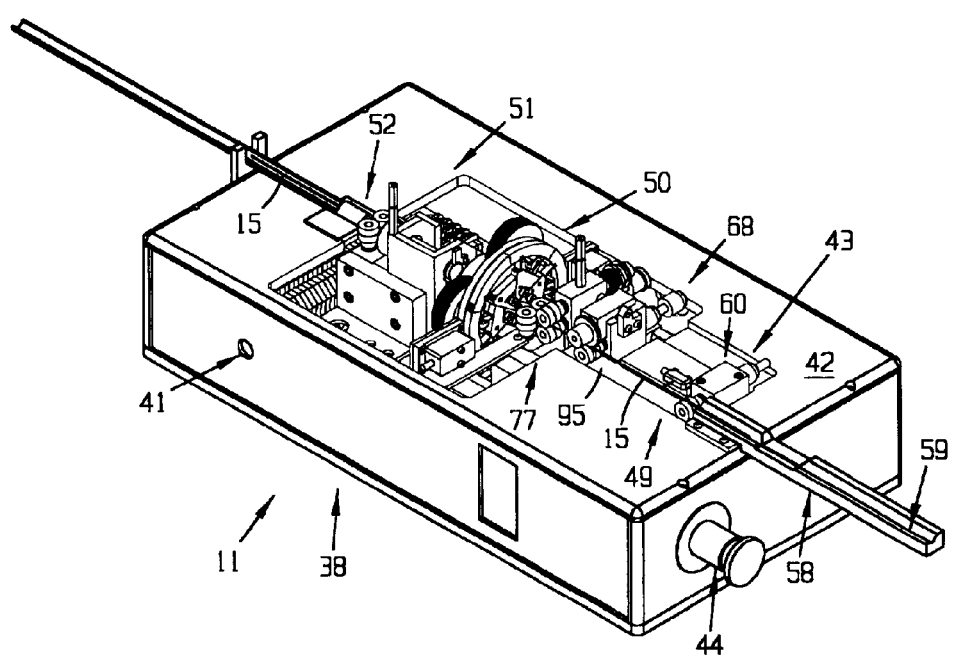
FIG. 2 is a perspective view of an embodiment of the swaging base unit of the present invention.
Figure 4:
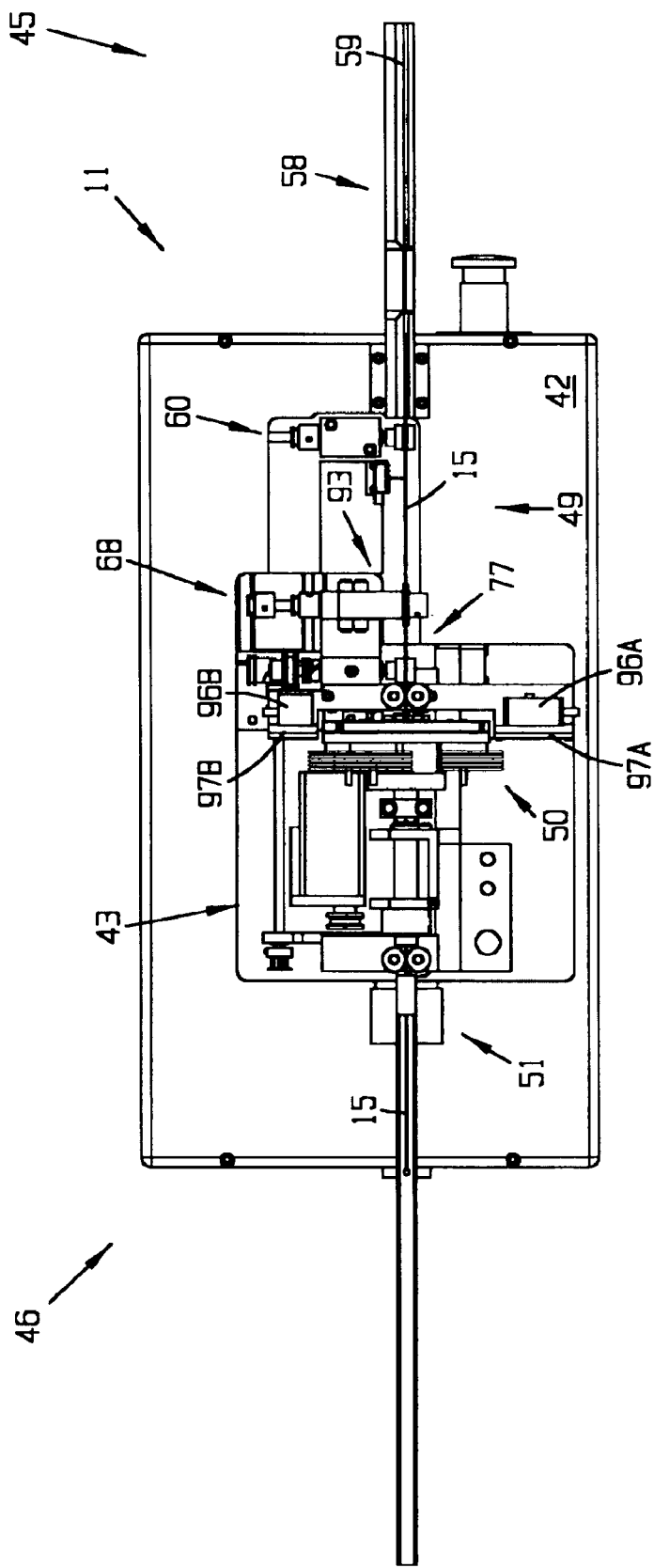
FIG. 4 is a top or plan view of the base unit.

The drawing Figures show preferred embodiments of the swaging system or swager 10, components thereof, and process of present invention. The swager system 10 is described below first in terms of its major structural elements and then in terms of its secondary structural and/or functional elements which cooperate to perform the preferred swaging function. The embodiments of the invention described are intended to be illustrative and not to be exhaustive or limit the invention to the exact forms disclosed. The embodiments are chosen and described so that persons skilled in the art will be able to understand the invention and the manner and process of making and using it.

The swaging system, apparatus and process is useful for connecting one material element, a swaged element, to another material element, a base element. In particular, it is useful for swaging bands, for example metal bands, to tubular structures, for example polymeric tubular structures, in a precise, substantially automated fashion. In particular, the swaging system, apparatus and process is beneficial for swaging marker bands to medical catheters, guide wires, stents and the like. In general however, the swaging system, apparatus and process may be used for forming or processing hollow or solid material or articles, particularly those constructed of malleable metals, such as tubes, casings, catheters, needles, rods, bars and wires, to reduce or increase the diameter, to create particular geometric shapes or profiles, to join or fasten, or to seal or finish such material or articles.

Referring to FIG. 1 one embodiment of the swaging system 10 includes a swaging base unit 11 and a control unit 12 which are connected via a cable master 39. The swaging base unit 11 processes articles and materials for swaging as is described in detail below. The control unit 12 controls the base unit 11. Although the base unit 11 and control unit 12 are shown as separate units, it is within the purview of the invention that they could be constructed in a single cabinet or housing. The control unit 12 includes a housing 26, a control panel 27, a display, and a meter 29. A bar code reader 30 is connected to input 32 in housing 26, via cable 31.

Referring to FIGS. 2–5, the swaging base unit 11 comprises an input handling system 49, a swaging head 50, an output handling system 51, and a catheter handling system drive system 52. The base unit 11 further preferably comprises a swaging head drive system 53 and a separate handling system drive system which drives both the input handling system 49 and the output handling system 51. These primary assemblies are housed in a housing 38 with a top deck 42 that has an open well area 43. Indicators 40 and 41 are located on the front face of the housing and a safety switch 44 is located on the input or proximal end of the housing 38. The base unit 11 has an input or proximal end 45 and an output or distal end 46. In general, during use, articles to be swaged are transported or conveyed substantially longitudinally, steamwise from the upstream input end 46 to the downstream output end. 46

Referring also to FIGS. 5–10, the input handling system or assembly 49 is disposed at the input or proximal end of the unit 11, on the top deck 42. This assembly 49 is responsible for mechanically receiving, holding, initially positioning, and transporting the articles or materials, for example a catheter and marker bands (which are preferably preloaded on the catheter), to be swaged to the swaging head 50. The input assembly 49 is communicatively connected to the control unit 12 to coordinate actuation of its subparts as is described in detail below.

The input handling assembly 49 includes an input guide 58, a first infeed roller assembly 60, a second infeed roller assembly 68, a positioning roller assembly 77, a first sensor 95, and a second sensor 96. The input guide 58 is a rectilinear block of a predetermined length with a coextensive linear guide slot 59 in the top surface, which has a V-shaped profile. The input guide block 58 is preferably constructed of a low friction polymeric material. The input guide block 58 is shown connected to the top deck 42, although it may alternatively be connected to the housing 38 or other elements of the base unit 11, either directly or indirectly by means known in the art.

In use, the articles to be swaged are placed by an operator or user by hand, or otherwise, in the guide slot 59 of the guide 58. The input guide 58 supports and aligns the articles to be swaged and permits them to be pulled along with low friction. Referring to FIGS. 19–22, preferred examples of an articles to be swaged include a catheter body 15, a first (distal) marker band 13, and a second, (proximal) marker band 14. The marker bands 14 and 13 are preloaded, for example by hand by an operator, onto the catheter body 15 and placed in zones "s" (which have a predetermined maximum length) near and distally with respect to the points at which they will be fastened to the catheter body 15 by swaging. The bands 13 and 14 have an inside diameter which is only slightly larger than the outside diameter of the catheter 15, so that the bands 13 and 14 tend to stay in place during processing by the system 10, by light friction forces. The catheter body 15 is a thin, elongated tubular structure with a central lumen 17, and a distal end tip 18. The typical catheter body 15 is constructed of a polymeric material or a combination of materials, and typical marker bands 13 and 14 are constructed of a radiopaque (blocks passage of x-rays) material. As is best shown in FIG. 21, marker bands 13 and 14 (only marker band 13 is shown) have an initial (unswaged) inner diameter which is slightly larger than the outside diameter of the catheter body 15. In some areas, a small gap 19 between the catheter body 15 and the bands 13 and 14 exists in this initial state. The catheter body 15 placed in the input guide 58 so that the tip 18 is disposed distally 46 with respect to the base unit 11.

Returning to FIGS. 2–10, the first infeed roller assembly 60 is disposed at the distal output end of the input guide 58, a predetermined distance therefrom. The first infeed roller assembly 60 engages the catheter 15 (including the preloaded bands 13 and 14) and transports it linearly, past the first sensor 95, to the second infeed roller assembly 68. The first infeed roller assembly 60 includes a rotatable roller 61 having a horizontally disposed shaft 63 rotabably connected in mounting block 62. Roller 61 is constructed of a suitable polymeric or other material. Roller 61 preferably has a V-shaped slot 65 which is vertically and horizontally aligned with the upstream guide slot 59 of the input guide 58 to receive the conveyed catheter body 15. Block 62 is connected to the housing 38 and other elements of the base unit 11 described below by a conventional bracket, but it may alternatively be connected to the top deck 42, housing 38 or other elements of the base unit 11 directly, or indirectly by other means known in the art such as a frame, mounting block, case, or the like. The shaft 63 extends out an opposite side of the block 62 to a pulley 64. Pulley 64 is communicatively connected to drive means preferably by a flexible belt (not shown for clarity) as is described in detail below.

The first sensor 95 is disposed a predetermined distance upstream from the second infeed roller assembly 68. The first sensor 95 senses the forward or leading tip of the catheter 15 as it passes being transported by the first infeed roller assembly 60.

The second infeed roller assembly 68 is disposed downstream from the first infeed roller assembly 60, a predetermined distance therefrom. The second infeed roller assembly 68 engages the catheter 15 delivered by the first infeed roller assembly 60 and linearly transports it to the positioning roller assembly 77. The second infeed roller assembly 68 includes a rotatable roller 69 having a horizontally disposed shaft 71 rotabably connected in mounting block 70. Polymeric roller 69 also preferably has a V-shaped slot 74 which is vertically and horizontally aligned with the upstream guide slot 65 of the first infeed roller assembly roller 61 to receive the conveyed catheter body 15. Block 70 is connected to the housing 38 and other elements of the base unit 11 described below by a conventional bracket, but such connection may be varied as is known in the art. The shaft 71 extends out an opposite side of the block 70 and pulleys 72 and 73 are connected to it. Pulley 73 is communicatively connected to drive means preferably by a flexible belt (not shown for clarity) as is described in detail below. Pulley 72 is communicatively connected to pulley 64 of first infeed guide roller assembly 60 and provides synchronized rotation thereto.

The positioning roller assembly 77 is disposed downstream from the second infeed roller assembly 68, a predetermined distance therefrom. It receives the catheter 15 from the second infeed roller assembly 68 and linearly transports the catheter 15 downstream, past the second sensor 96a/b, to the swaging head 50. The positioning roller assembly 77 includes a pair of rotatable horizontal rollers 78a and b, each of which has a horizontally disposed parallel shafts 80a and b rotabably connected in mounting block 81, and a pair of rotatable vertical rollers 79a and b, each of which is has a vertically disposed, parallel shafts 83a and b connected in mounting block 85. Polymeric rollers 78a/b and 79a/b also preferably have V-shaped slots which is vertically and horizontally aligned with each other and with the upstream guide slot 74 of the second infeed roller assembly roller 68 to receive the conveyed catheter body 15. Blocks 81 and 85 are connected to the housing 38 and other elements of the base unit 11 described below by a conventional bracket, but such connection may be varied as is known in the art. The shaft 71 extends out an opposite side of the block 70 and pulleys 72 and 73 are connected to it. Pulley 73 is communicatively connected to drive means preferably by a flexible belt (not shown for clarity) as is described in detail below. Pulley 72 is communicatively connected to pulley 64 of first infeed guide roller assembly 60 and provides synchronized rotation thereto.

The second sensor 96a/b is disposed a predetermined distance downstream from the positioning roller assembly 77 and a predetermined distance upstream from the swaging head 50. The second sensor 96 senses the forward or leading tip of the catheter 15 as it passes being transported by the positioning roller assembly 77.

Referring to FIGS. 2–5, the swaging head 50 is disposed generally longitudinally centrally in the swager base unit 11, a predetermined distance downstream from the positioning roller assembly 77 and the second sensor 96. It preferably has a circular, disk shaped configuration with its center aligned for reception of the catheter 15 delivered by the input handling assembly 49 elements described above. The swaging head 50 is communicatively connected to the control unit 12 and cooperates with the input handling assembly 49 and the output handling system 51 to swage and output a swaged article. In general, the catheter 15 and bands 13 and 14 preloaded (but unswaged) at certain locations on the catheter 15 body are sequentially, linearly advanced predetermined distances to align the respective preloaded bands 13 and 14 with the swaging head 50. The swaging head 50 is then actuated to first preferably move each respective band 13 and 14 to precise respective points on the catheter 15 body, and second to respectively swage the bands 13 and 14 at such points, whereby they are firmly fixed in position at such points. The fully swaged product 15 is then linearly advanced to the output end 46 by the output handling assembly 51. During band movement, the swaging head 50 gently engages the band to hold it while the catheter body 15 is advanced by the positioning roller assembly 77. During band swaging, the swaging head rotates and simultaneously undergoes a predetermined sequence of radial band impacting and band releasing movements. This results in precise, gentle radial compression of the bands 13 and 14 on the catheter.

Referring also to FIGS. 6–14, the swaging head 50 generally comprises a die plate 100, an actuation or closer plate 101, a plurality of actuators 102a–d, and a support assembly 103. The support assembly 103 is coupled to the closer plate 101 and holds the head 50 and place and rotates it. The die plate 100 is coupled to the closer plate 101 so that it can rotate relative to it a small predetermined degree. The actuators are mounted on the closer plate 101 and communicatively connected to the die plate 100 and function to rotate the die plate 100 relative to the closer plate 101.

Referring also to FIGS. 15–18, the die plate 100 of the swaging head 50 preferably has a circular, disk-like configuration. It is preferably constructed of a metallic material. The die plate 100 has a ring shaped, circumferential base 1108 and at least three, and preferably six, die segments 107a–f which are disposed within the ring of the base. Each die segment 107 is linked to each other as is described in detail below, and to the base 108 via a radial flexure 109a–f. Each radial flexure 109 preferably is connected to the base 108 in a flexure slot 130 in the base 108. A center aperture 112 is disposed at the center of the die plate 100. The swaged article, for example a catheter 115 and marker bands 13 and 14 pass though the center aperture 112.

Figure 16:
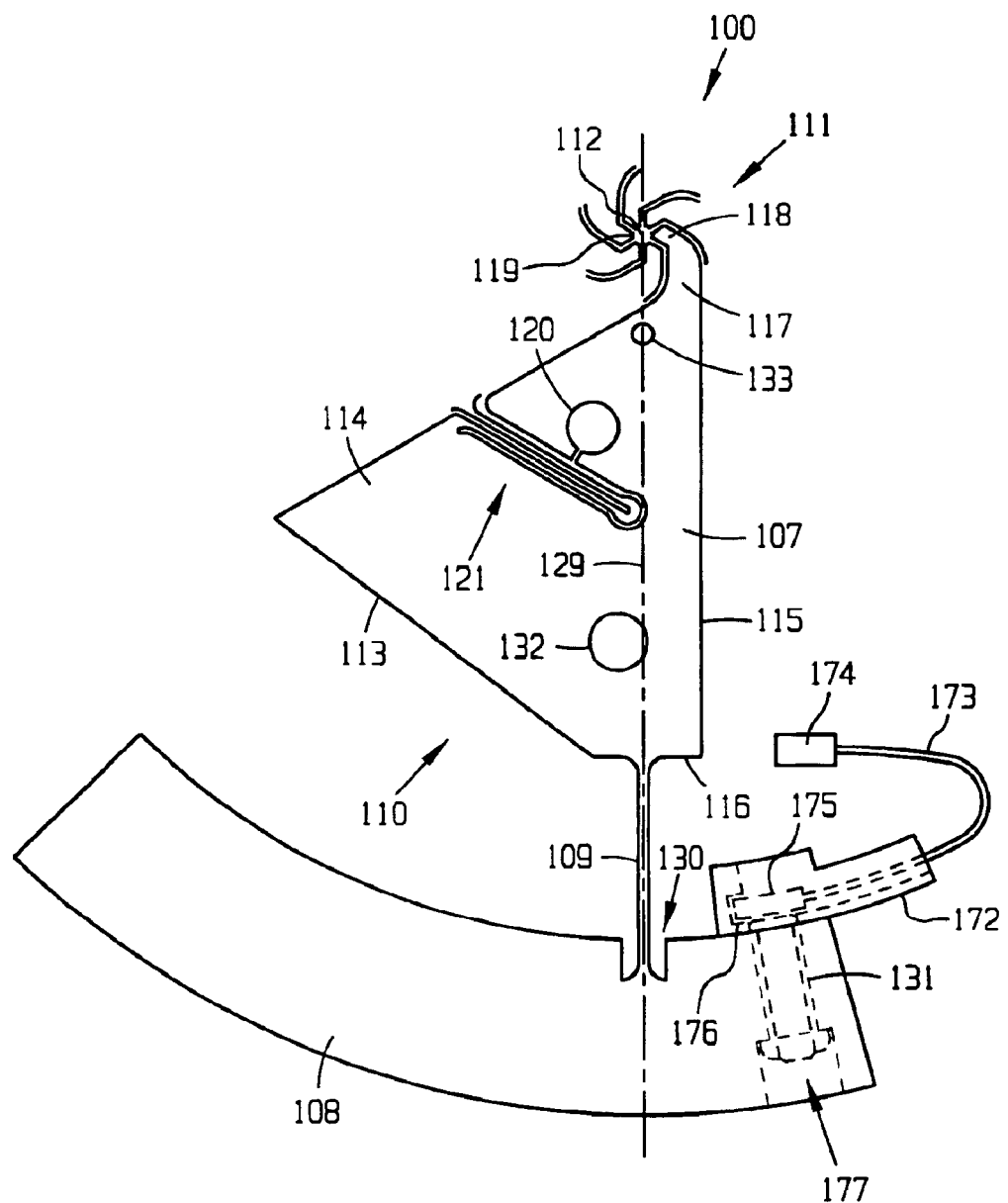
FIG. 16 is a top view of a portion of the swaging die plate showing an embodiment of the swaging segment of the present invention.
Figure 17:
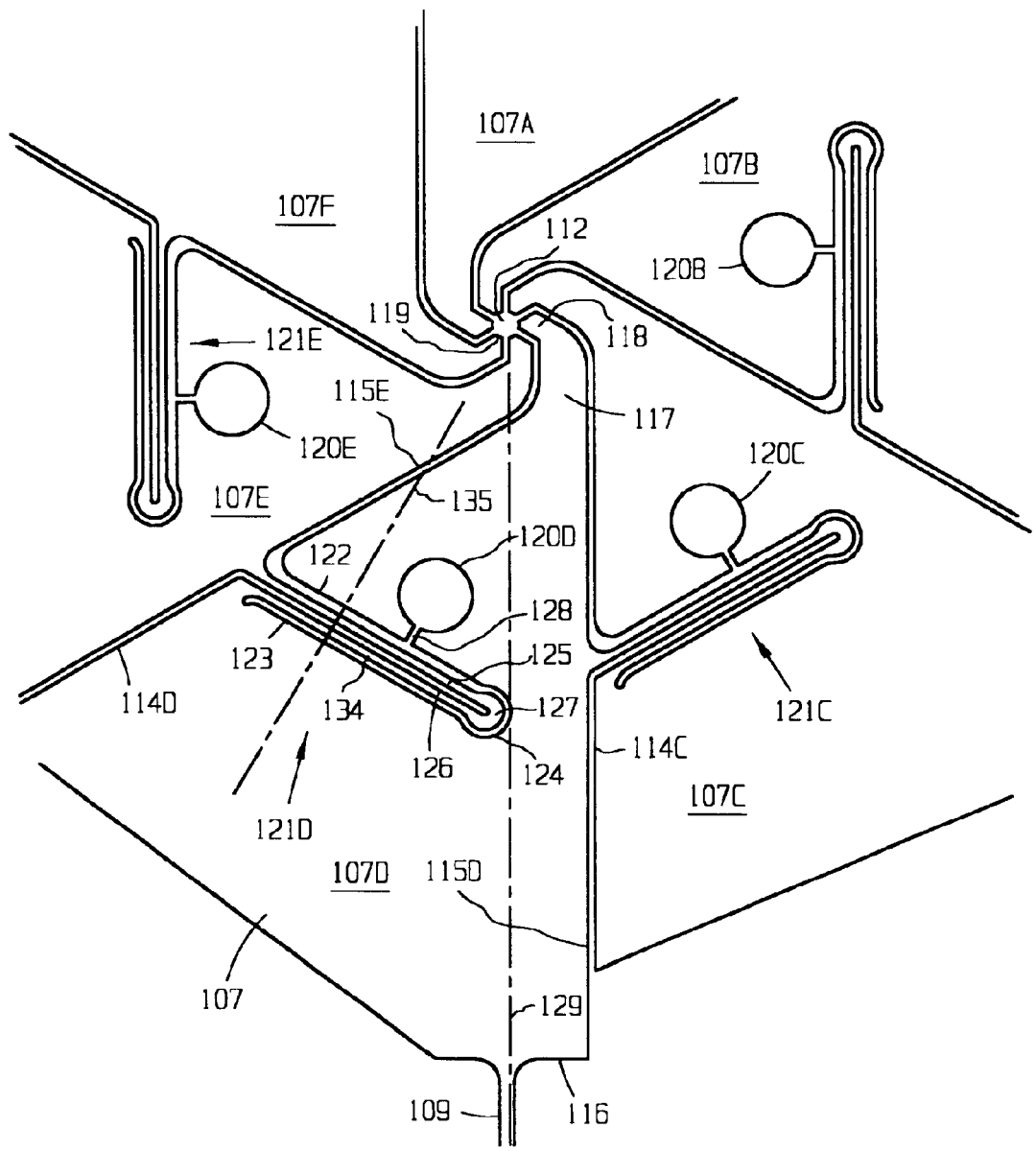
FIG. 17 is an enlarged view of the swaging segment.

As is best shown in FIGS. 16 and 17, each die segment 107 (107c, d and e are shown for example) has a generally thin, linear and somewhat flat, triangular configuration with a proximal end 110 disposed near the base 108 and a distal end 111 disposed near the center aperture 112. A proximal face 113 is oriented hear the base 108. A female face 114 is disposed near one neighboring segment and a male face 115 is disposed near an opposite neighboring segment. At the proximal end 110, radial flexure 109 extends from proximal face 116. Major arm 117 and minor arm 118 are disposed at the distal end 111 of each die segment 107. A swaging surface 119 of a predetermined profile or configuration, in the preferred embodiment a curve of predetermined dimensions and radius, is disposed at the distal end of the minor arm 118. This surface 119 impacts the article to be swaged. The profile of the surface 119 is variable depending upon the particular article and swaging application desired. Circumferential flexure 121 (121d for example) is formed by an inner beam 125 extending from the male face 115e and coupling at curved intersection 127 to an outer beam 126 formed in the body of the segment 107d. The beams are separated by outer slot 123 joined by curved intersection 124 to inner slot 122. Inner slot 122 in communicatively connected to a space between female face 114d of the segment 107d and the male face of adjacent segment 107e, which space extends to center aperture 112. A center slot 134 is communicatively connected to a space between female face 114 and male face 115e of adjacent segment 107e, which extends proximally and separates the segments 107d and 107e. Inner slot 122 is communicatively connected to pivot aperture 120d via pivot slot 128. Each die segment 107a–f is thus directly connected to its two neighboring die segments via the structure of the circumferential segments 121. This structure, in combination with the connections of the die segments 107 to the common base via the radial flexures, indirectly communicatively connects each die segment to all other die segments in the die plate 100.

Referring to FIG. 16, optional aperture 132 is for mounting of an optional heating element (not shown), and optional aperture 133 is for mounting of an optional sensor, such as a force measurement transducer (not shown).

Figure 11:
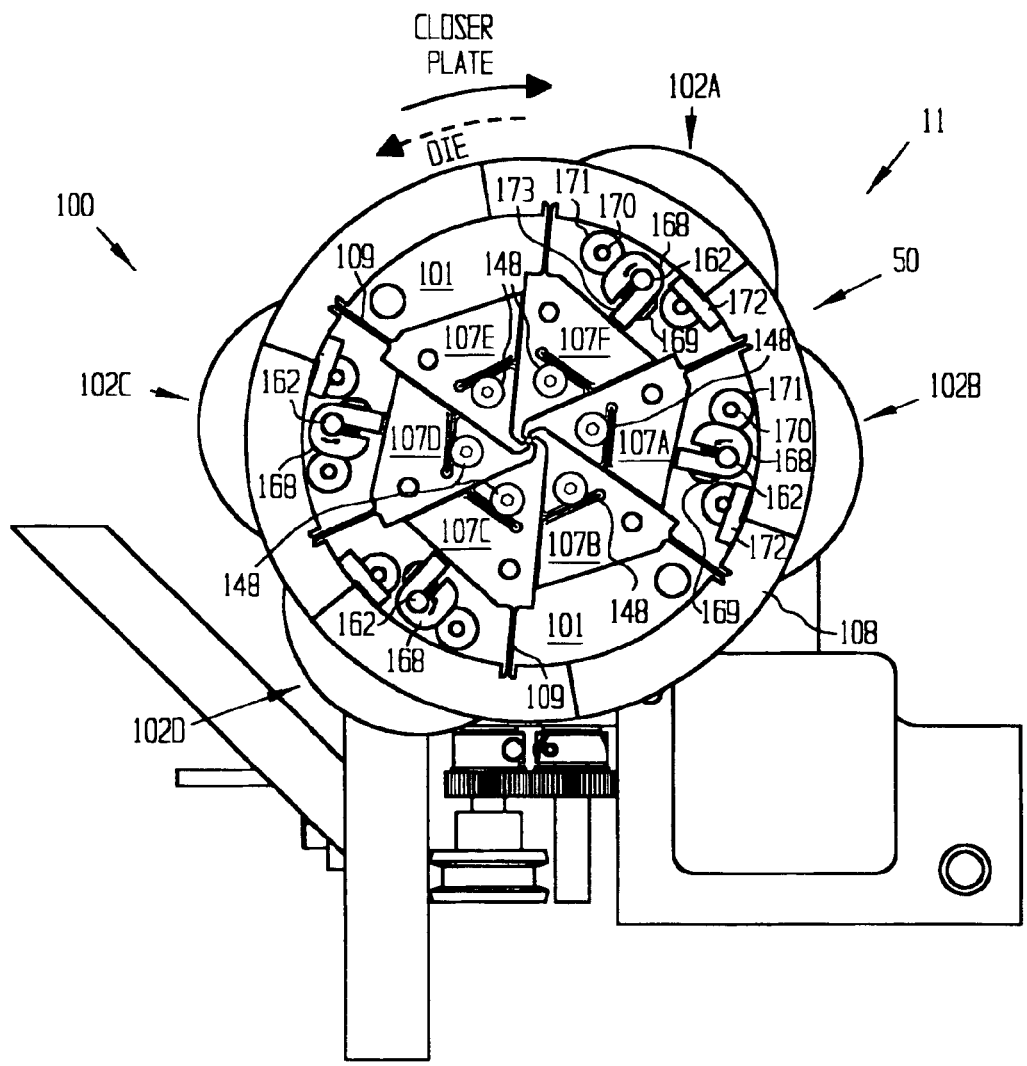
FIG. 11 is a proximal view of an embodiment of the swaging head of the present invention.
Figure 14:
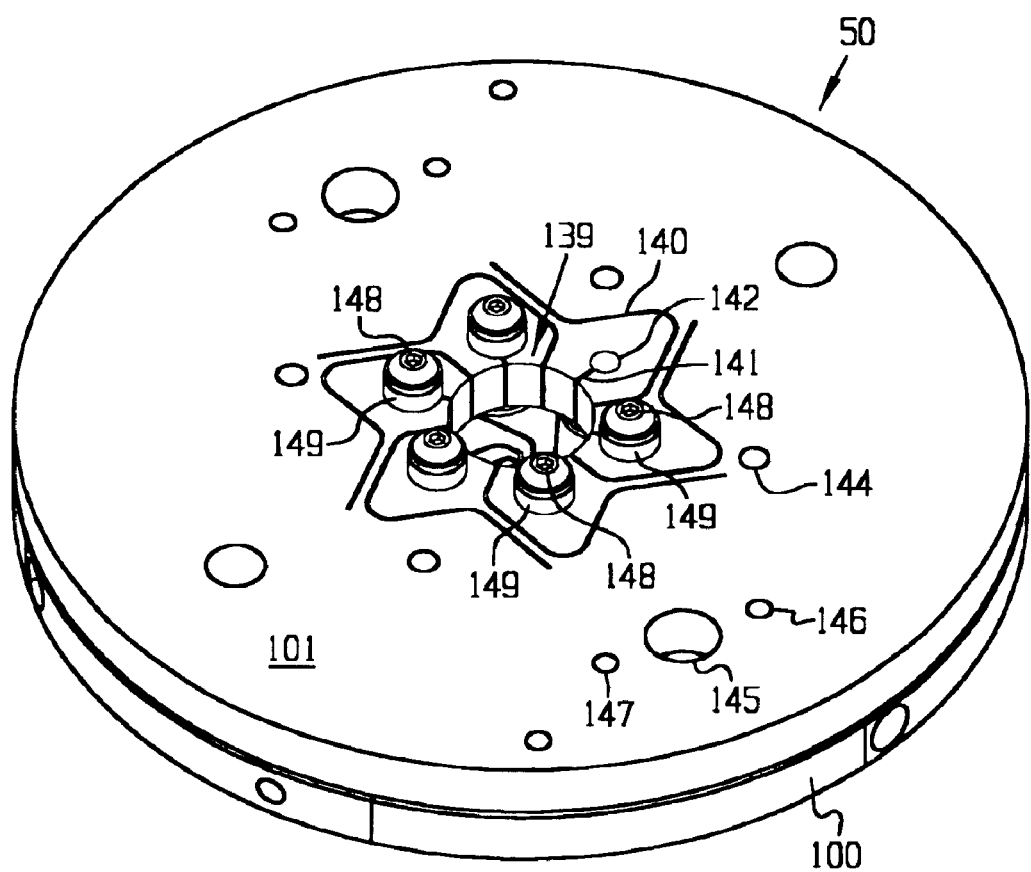
FIG. 14 is a perspective view of an embodiment of the closing plate of the present invention attached to an embodiment of the swaging die plate of the present invention.
Figure 15:
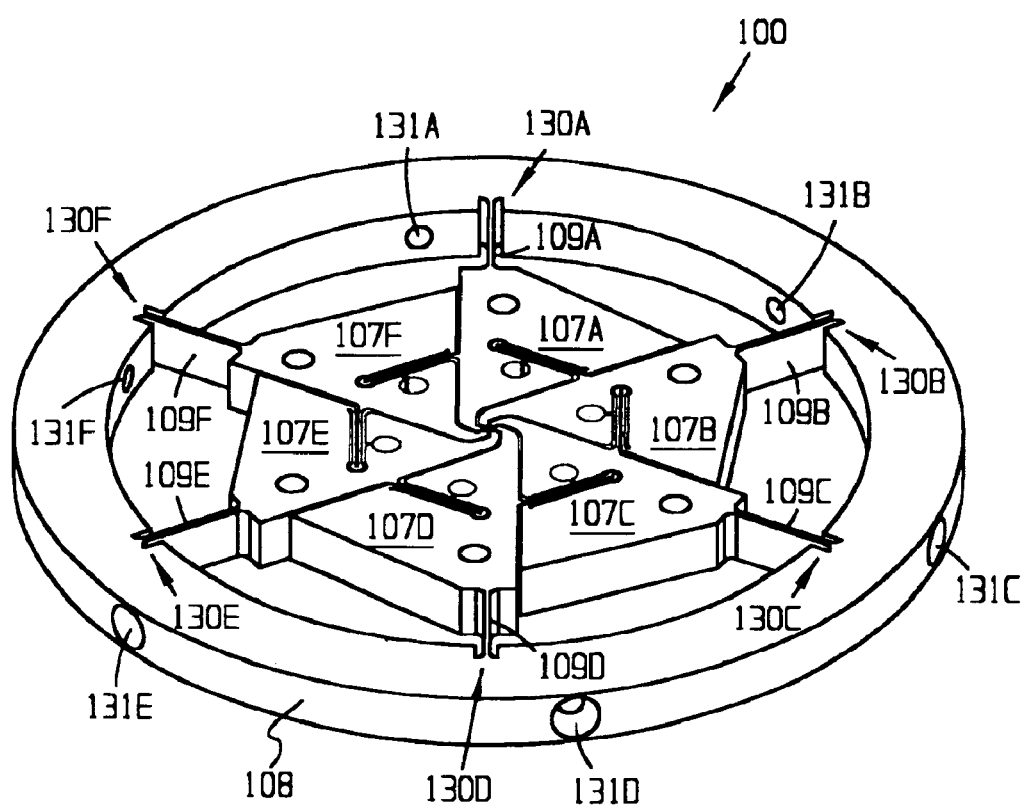
FIG. 15 is a perspective view of an embodiment of the swaging die plate of the present invention.

Referring also to FIGS. 11 and 14, closure shafts 148 extend through pivot apertures 120 and are fixed in position relative to the die segments 107 in the closure plate 101 (via securement cap 149). During action of the die plate 100, force is applied (as described below) on the base 108 to drive the base 108 in a counter-clockwise direction as viewed in FIG. 11. Force from the base 108 is applied to the die segments 107 via bending or pivoting of the radial flexures 109. As the die segments 107 are correspondingly driven they pivot around the closure shafts 148 disposed in pivot apertures 120. The pivot apertures 120 are disposed off of the centerline 129. The longitudinal axis of radial flexure 109 is aligned with the center aperture 112 (See centerline 129) to provide pivotal movement of the die segments 107 relative to the center aperture 112 during die plate actuation. The major and minor arms 117 and 118 are configured to orient the swaging surface 119 to move towards the center of the center aperture 112 during die plate 100 actuation. The circumferential flexures 121 are configured and aligned substantially perpendicular to a line 135 extending from the center aperture 112. This configuration of the circumferential flexure 121 permits movement between adjacent die segments 107 (e and d, for example) which is parallel to this line 135 (i.e. perpendicular to the beams 125 and 126 of the circumferential flexures 121) and minimizes movement between adjacent die segments 107 which is perpendicular to the line 135 (i.e. parallel to the beams 125 and 126) during die plate 100 actuation. This in turn causes the die segments 107 to move in a precise and predictable fashion with respect to each other to control movement of the swaging surfaces 119 and closure of the central aperture 112 for swaging purposes.

Figure 18:
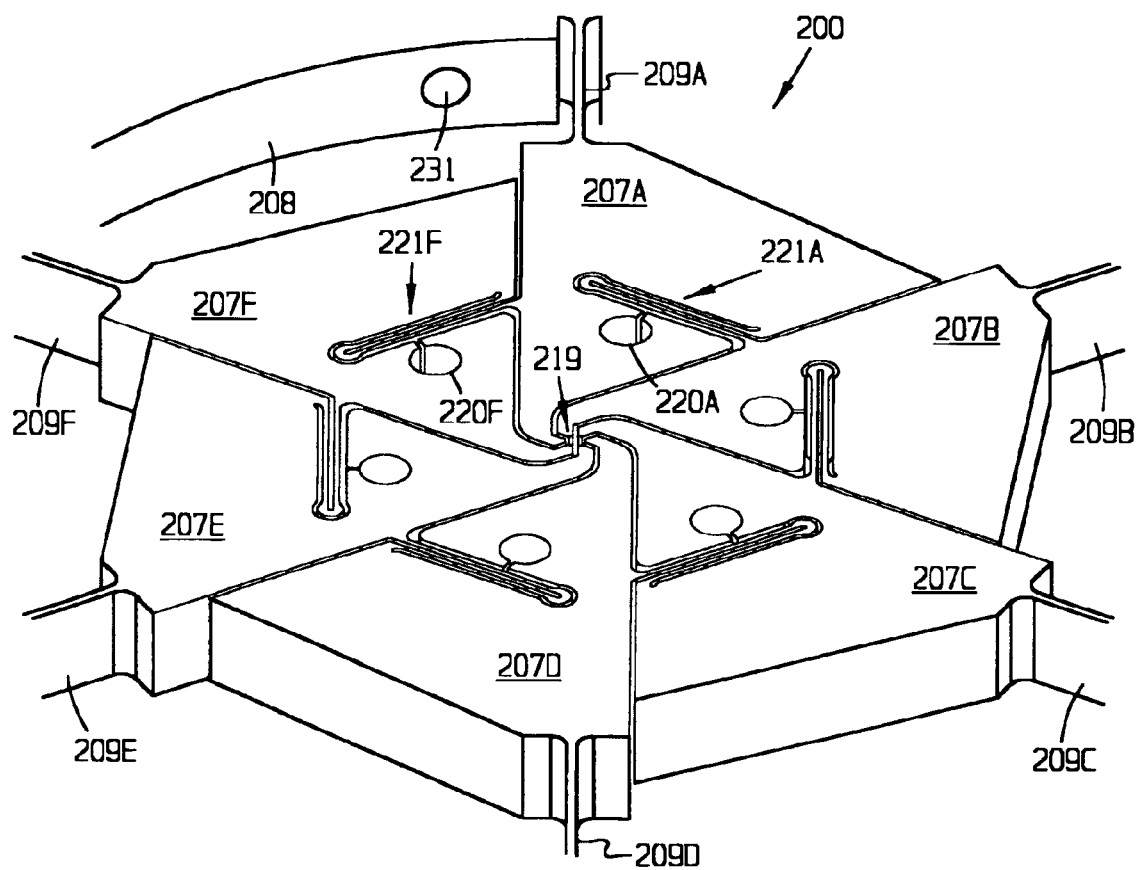
FIG. 18 is a perspective view of a portion of an alternative embodiment of a swaging segment.
Figure 19:
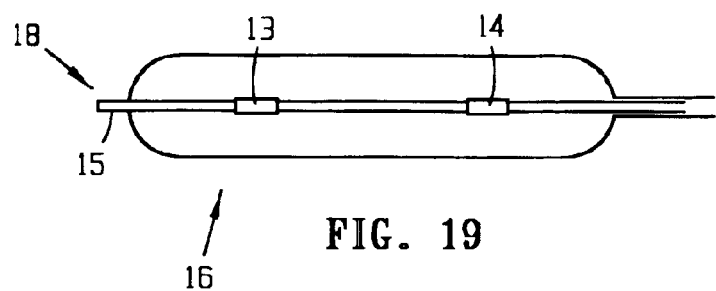
FIG. 19 is a simplified illustration of a medical balloon-type catheter, which is constructed using the system, apparatus and method of the present invention.

FIG. 18 shows an alternative embodiment of the die plate 200 showing an alternative die segment 207 geometry and major and minor arm configuration.

Figure 13:
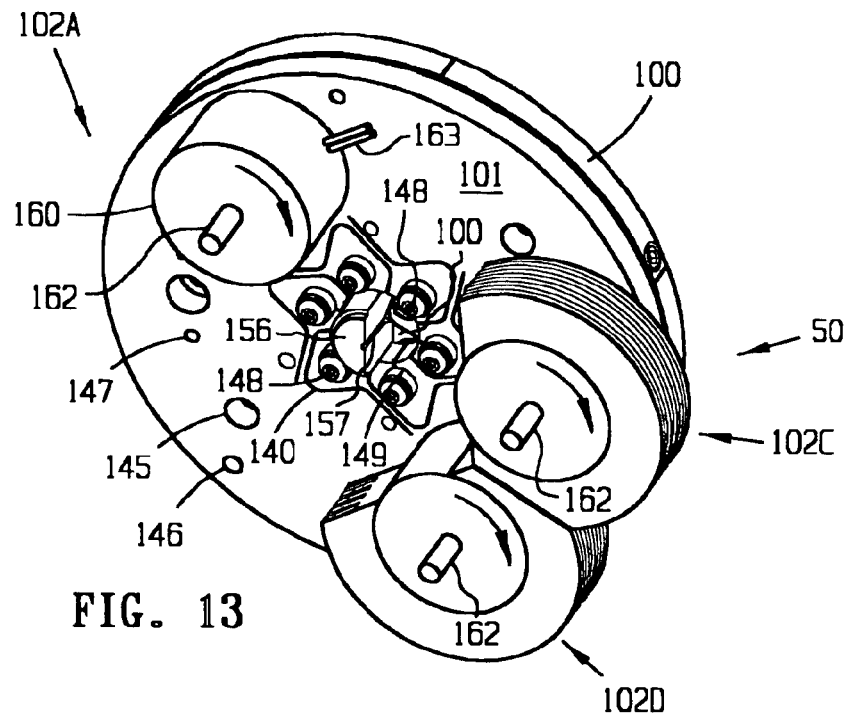
FIG. 13 is a distal view of the swaging head with elements removed for clarity.

Referring also to FIGS. 13 and 14, the closer plate 101 of the swaging head 50 preferably has a circular, disk-like configuration with dimensions substantially equivalent to the die plate 100. It is preferably constructed of a metallic material. A central aperture 139 is centrally disposed for movement of the swaged article therethrough. Closure shafts described above extend through apertures (not shown) which are aligned with pivot apertures 120 of the die segments 107. Major flexure slots 140 extend from the center aperture 139 in a predetermined configuration. Minor flexure slots 141 extend from the center aperture 139 radially to the closure shaft apertures (not shown). Shaft caps 149 are disposed on the end of the closure shafts 148. Distal mounting block apertures 144, actuator shaft apertures 145, and actuator connector apertures 146 and 147 are disposed in the closure plates 101.

Figure 12:
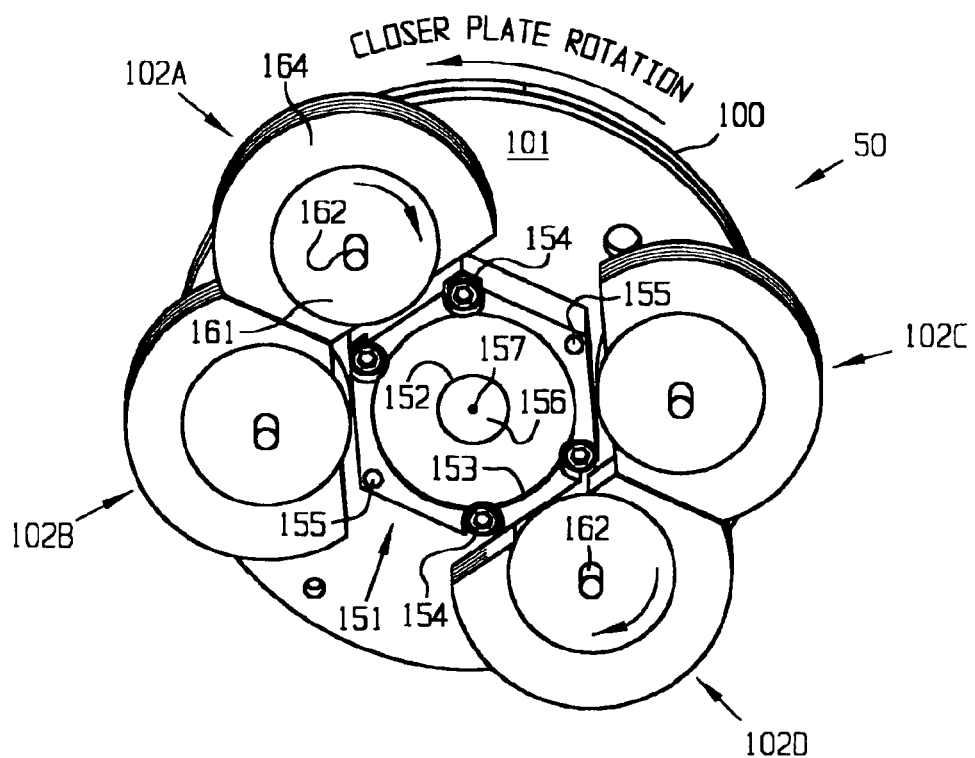
FIG. 12 is a distal view of the swaging head.

A distal mounting block 151 is shown in FIG. 12 connected to the closure plate 101 via connectors 154 which mate with distal mounting block apertures 144. The distal mounting block 151 has a central aperture 152 and an inset rim 153. Drive shaft connection apertures 155 are disposed on the mounting block 151. A funnel 156 with a central aperture 157 is disposed in the center aperture 139 of the closing place 101 and the center aperture 152 of the mounting block 151. The distal mounting block 151 is for connection of a drive shaft thereto for support and rotation of the closure plate 101 and attached die plate 100. Optionally., the distal mounting block may be constructed to provide a quick release magnetic or other attachment of the swaging head to the drive shaft.

Figure 6:
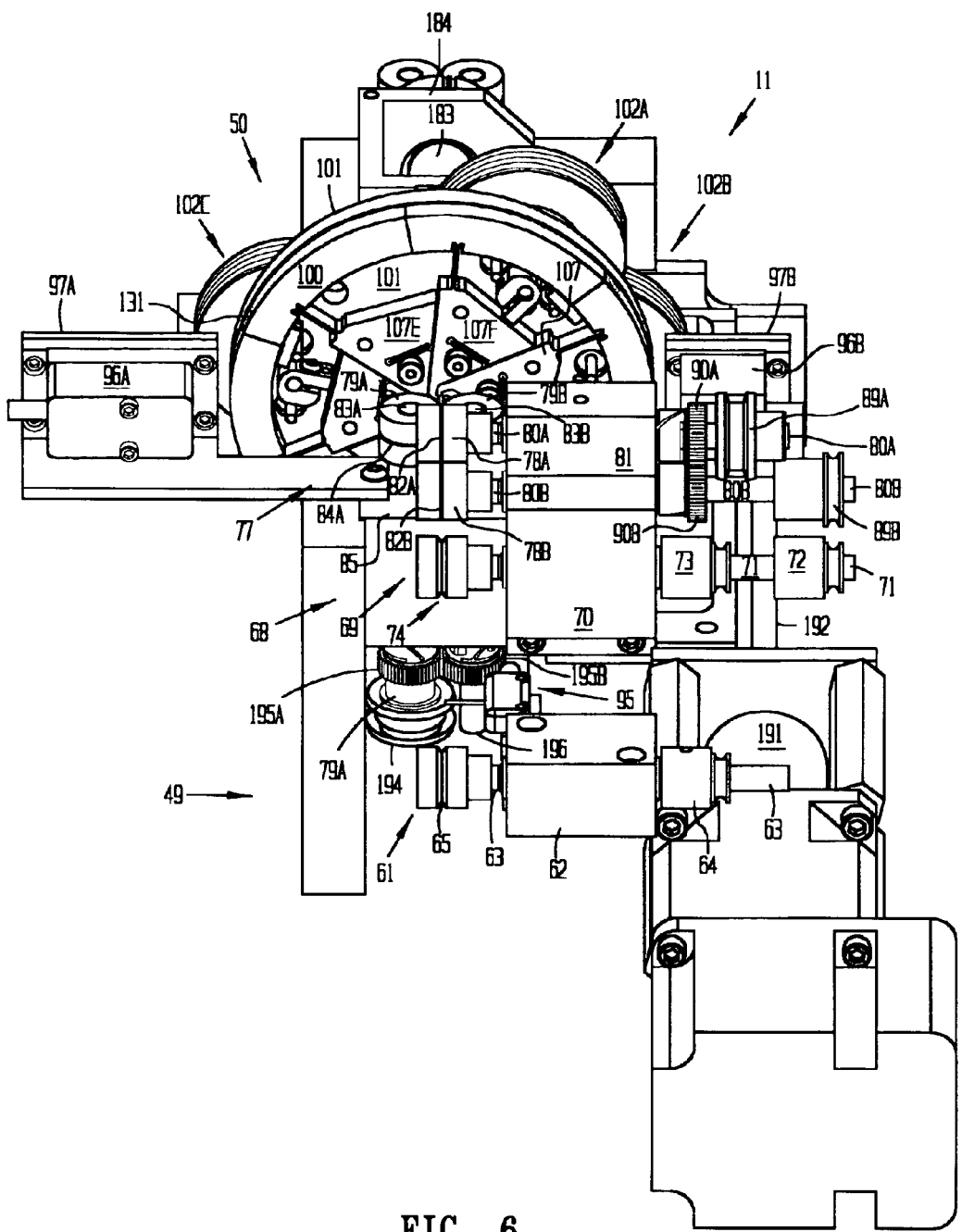
FIG. 6 is a view of the input or proximal end of the base unit.
Figure 7:
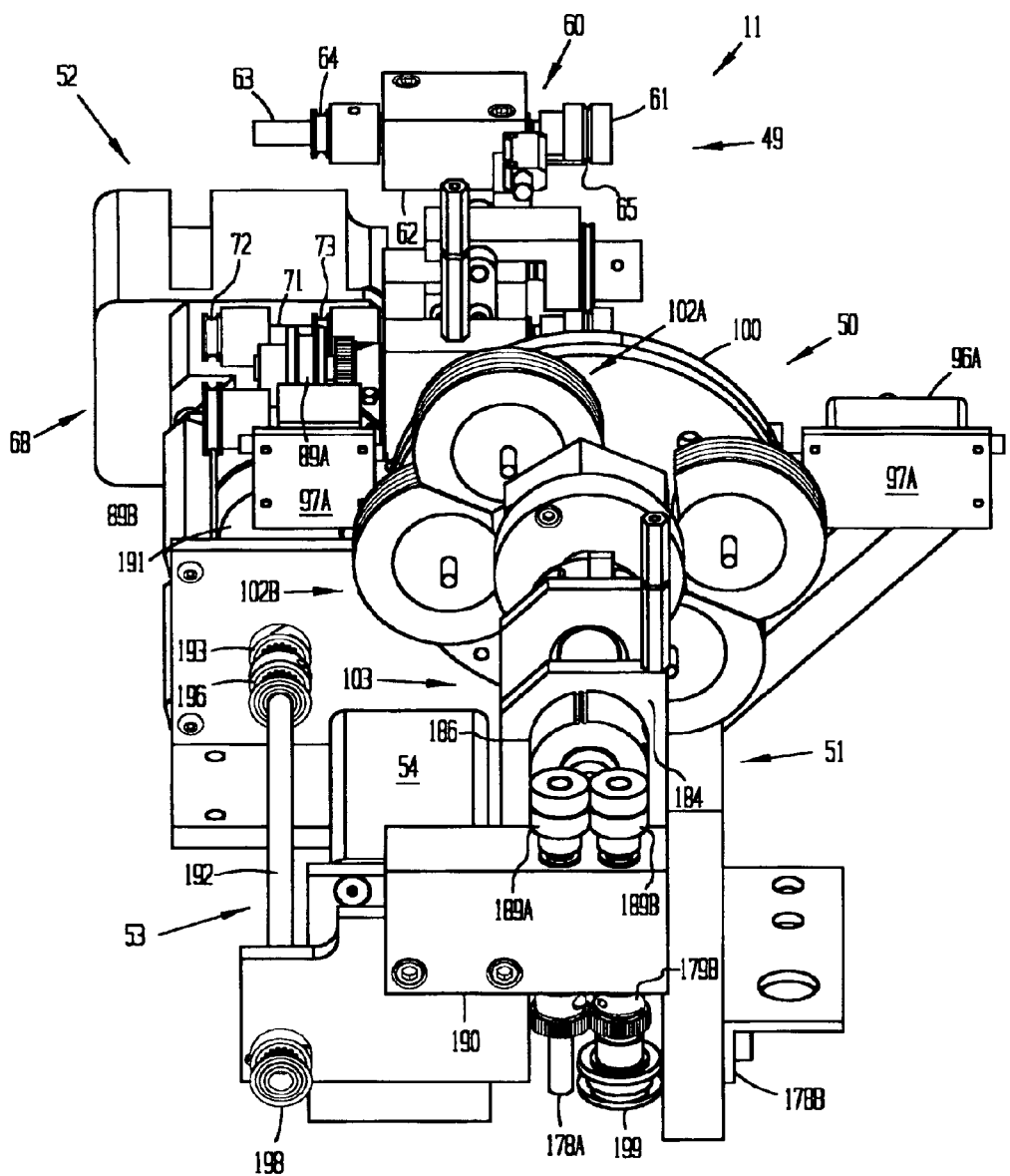
FIG. 7 is a view of the output or distal end of the base unit.

Referring to FIGS. 6, 7, 11–13 and 16, the actuators of the swaging head 50 comprise at least one., and preferably a plurality (for example four) actuator assemblies 102a–d which are connected to the closing plate 110 and the die plate 100. As is best shown in FIGS. 7, 12 and 13, each actuator assembly 102 comprises an actuator or motor 161a–d connected and fixed to the closing plate 101 via connectors 170 disposed through actuator connector apertures 146, an actuator shaft 162 connected to and drivable by the motor 161a–d, and extending proximally through the actuator shaft apertures 145 a predetermined distance to the proximal side of the closing plate 101, power supply wiring 163a–d communicatively coupled to the motor 161 and the control unit 12, and heat dissipation fins 164a–d or the like coupled to the motor 162. As is best shown in FIGS. 6, 11 and 13, each actuator assembly 102 further comprises a clamp collar 168 connected to the proximally extended actuator shaft 162 and an associated clamp collar screw 169, an actuator cable 173 connected to the clamp collar 168, and a die plate connection block 172. As is best shown in FIGS. 11 and 16, the die plate connection block is connected to the die plate 100 base 108 by connector 177 in base aperture 131. Actuator cable 173 has proximal end 174 which is connected to the clamp collar 168 and distal end 175 which is connected in well or recess 176 of connection block 172.

In use, to actuate the swager head 50 to close the radially move engagement surfaces 119 to close aperture 112 for both band grasping or band swaging purposes power is supplied to motor 160 which rotates drive shaft 162 (counter clockwise as viewed from FIG. 11 and clockwise as viewed from FIGS. 12 and 13). Clamp collar 168 turns with actuator shaft 162 and pulls attached actuator cable 173. This causes attached connection block to pull die 100 base 108 counter clockwise (as viewed from the proximal or input end (FIG. 11)). The rotating die base 108 applies force on the die segments 107a–f via their respective radial flexures 109 and the die segments 107 pivot around shafts 148 in apertures 120. Tile structure and configuration of the pivoting die segments 107a–f yield radial inward movement in their respective swaging surfaces 119a–f. The radial force is adjustable depending upon function, for a grasping force for marker band positioning, or a swaging force for marker band impacting, and material specifications. Additionally, the swaging head 50 may be stationary or rotating during die plate actuation. In a grasping mode, for example where the swaging head 50 is holding a marker hand 13 or 14 while the catheter 15 is advanced to position the band on the catheter, the swaging head 50 is stationary. In a swaging mode, the swaging head is rotated while the swaging surfaces 119 are simultaneously pulsed and released to uniformly impact marker bands about their periphery.

Referring to FIGS. 2–5, the output handling system or assembly 51 is disposed at the output or distal end of the unit 11, on the top deck 42. This assembly 51 is responsible for mechanically receiving and transporting the combined, swaged article, for example a catheter and connected marker bands, from the swaging head 50 to the distal end 46 of the system 10 At this point, the swaged product may be removed by an operator or delivered to ancillary materials handling or processing equipment. The output assembly 51 is communicatively connected to the control unit 12 as is described in detail below.

Referring also to FIGS. 7–10, the output handling assembly 51 includes a drive shaft 183 supported by a drive shaft support 184. Drive end 186 has gear teeth for coupling with a drive belt. A locating collar 188 is clamped to the drive shaft 183 to supply information about the rotational position of the shaft 183 to the control system 12. The drive shaft 183 rotates the swaging head 50 (clockwise as viewed from the proximal end in FIG. 11 and counter-clockwise as viewed from the distal end in FIG. 12) during a swaging mode) The drive shaft is hollow and aligned with the central aperture 112 of the swaging head 50 to receive the swaged catheter 15 conveyed by the input handling assembly 49. The output handling assembly 51 further comprises an output funnel 187 disposed downstream of the drive end 186, and an egress roller assembly disposed a predetermined distance downstream of the output funnel 187, preferably consisting of egress rollers 189a and b mounted in block 190.

Referring to FIGS. 6–10, the input/output handling system drive system preferably comprises a motor 191 communicatively connected to the control system 12 and a drive shaft 192 connected to the motor 192 extending rearwardly. A first pulley or pulley-like connector 193 on the drive shaft 192 is connected to a generally laterally and horizontally extending belt (not shown for clarity) which is also coupled to a vertical positioning roller assembly connector 194, which drives vertical positioning roller shaft 79a directly and shaft roller shaft 79b via gears 195a and b. A second connector 196 on the drive shaft 192 is connected to a vertically extending belt (not shown form clarity) which is also coupled to horizontal positioning roller assembly connector 89a, which drives horizontal positioning roller shaft 80a directly and roller shaft 80b indirectly via gears 90a and b. Connector 89b is also connected to shaft 80b. A belt (not shown for clarity) runs proximally and horizontally from connector 89b to couple with connector 72 on second infeed roller shaft 71 and supply drive power thereto. Also connected to shaft 71 is a connector 73. A belt (not shown for clarity) runs further proximally and horizontally from connector 73 to couple with connector 64 on first infeed roller shaft 63 and supply drive power thereto. Drive shaft 192 further has a third connector 198 disposed at its distal or output end. A belt (not shown for clarity) runs laterally and horizontally to coupled to egress roller connector 199 attached to egress roller drive shaft 178b. This also supplies drive power to egress roller drive shaft 178 via gears 179a and b.

Figure 8:
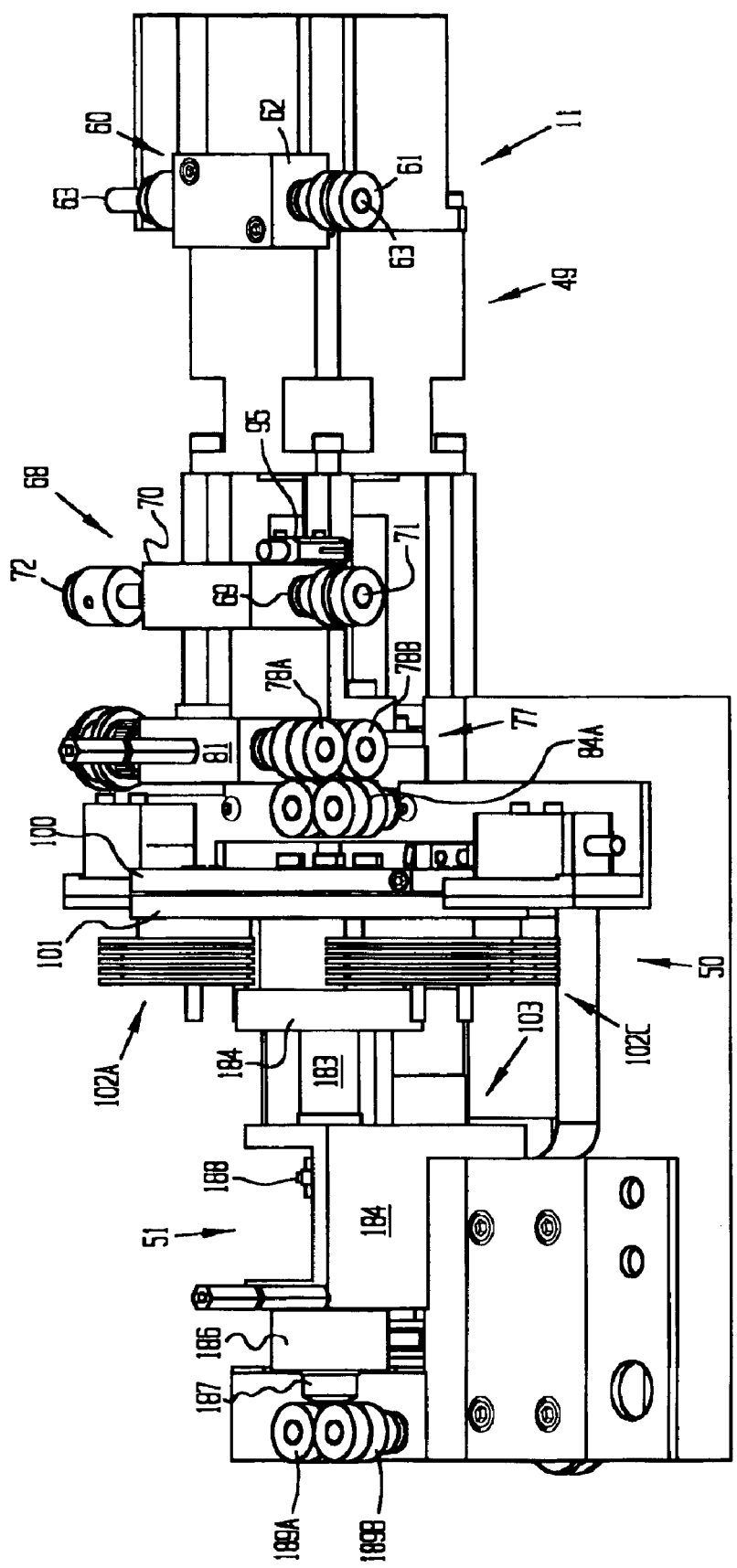
FIG. 8 is a further perspective view of the base unit.
Figure 9:
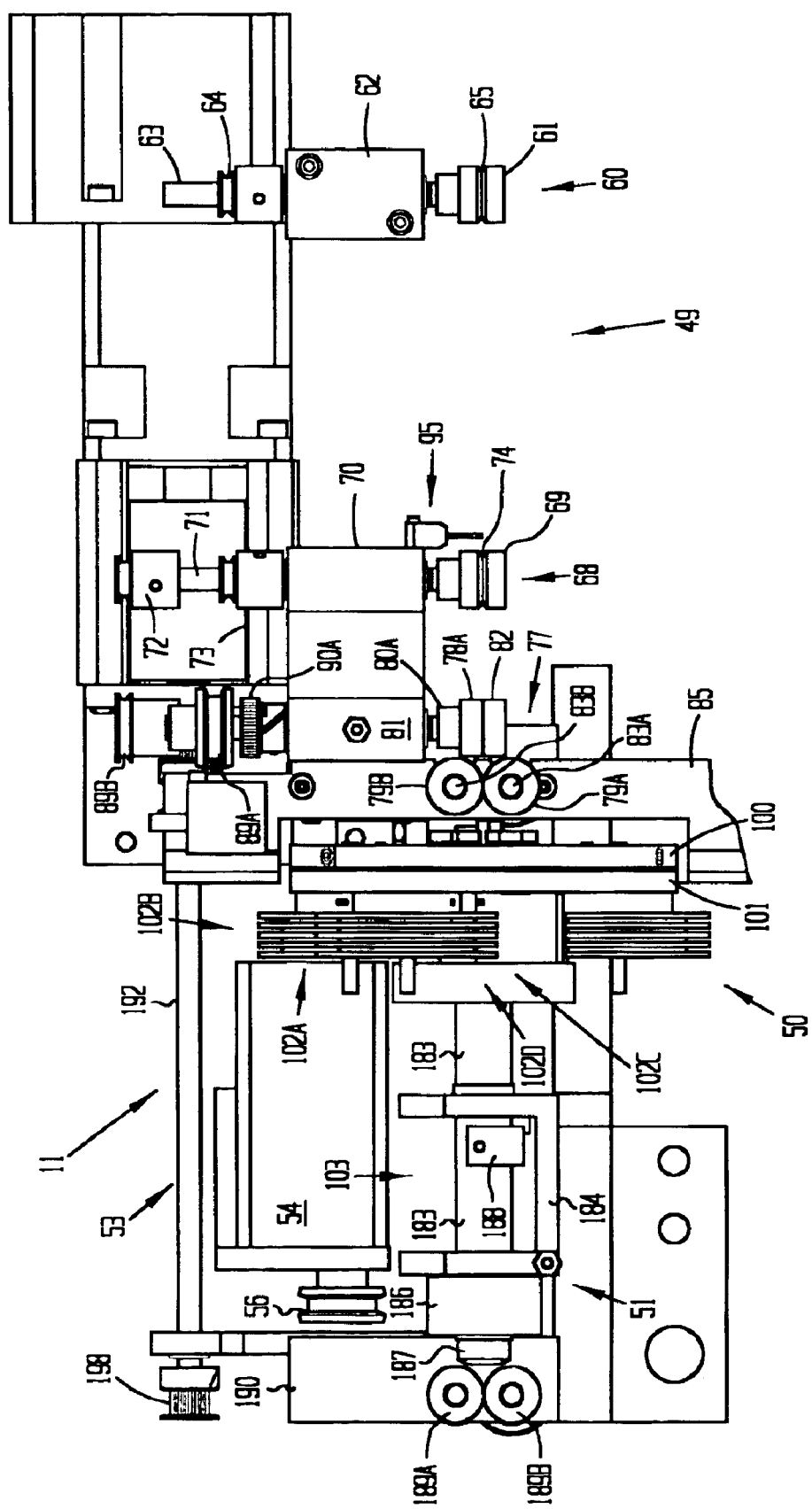
FIG. 9 is a top view of the base unit.
Figure 10:
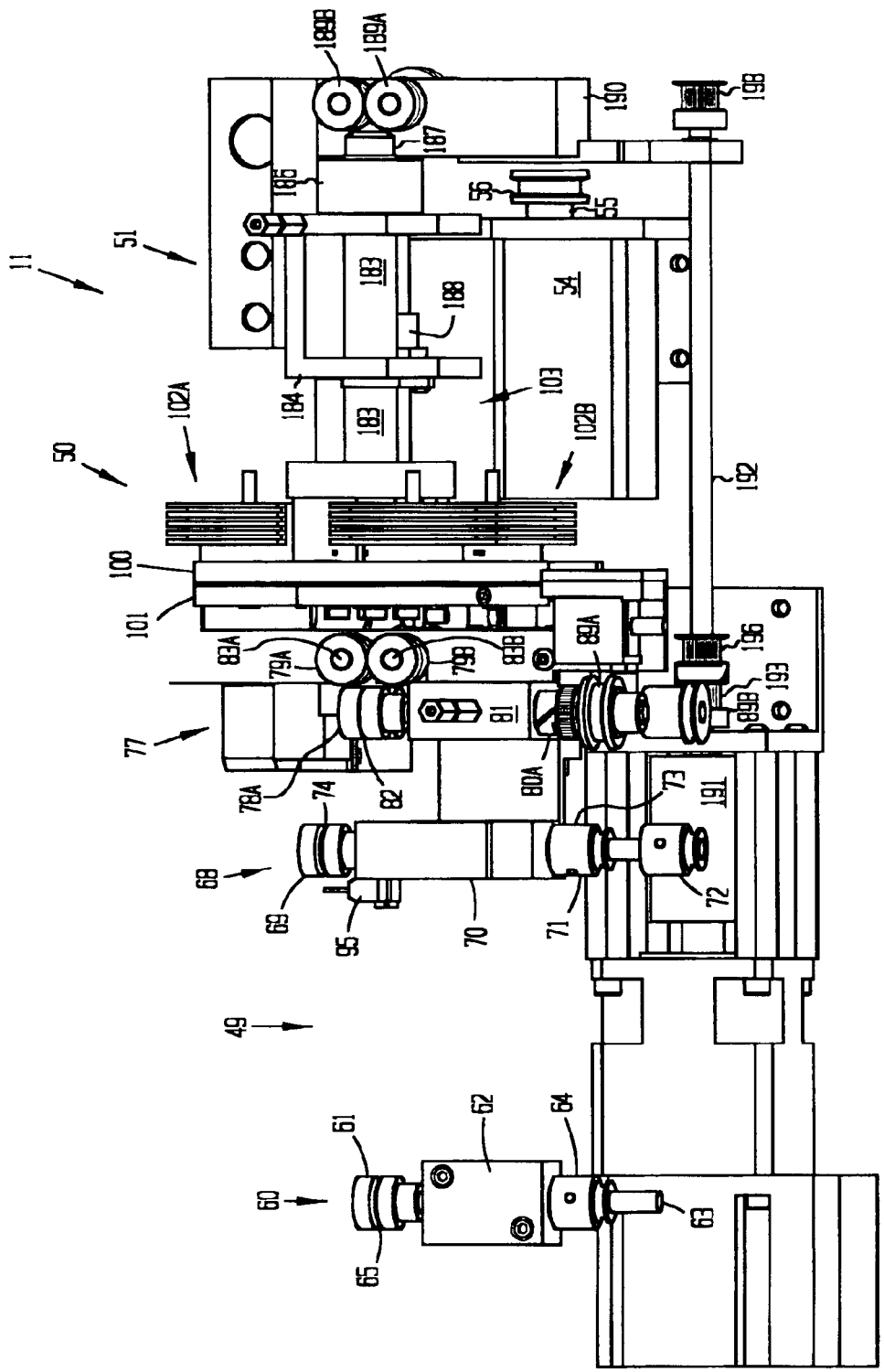
FIG. 10 is a further perspective view of the base unit.

Referring to FIGS. 7 and 8, the swaging head drive system 53 preferably comprises a motor 54 communicatively connected to control unit 12, a drive shaft 55 extending from the motor 54, a pulley or pulley-like connector 56 connected to the drive shaft 55 and a belt (not shown for clarity) which extends from the connector 56 laterally to mate with the drive end 186 of the drive shaft 183.

Figure 23:
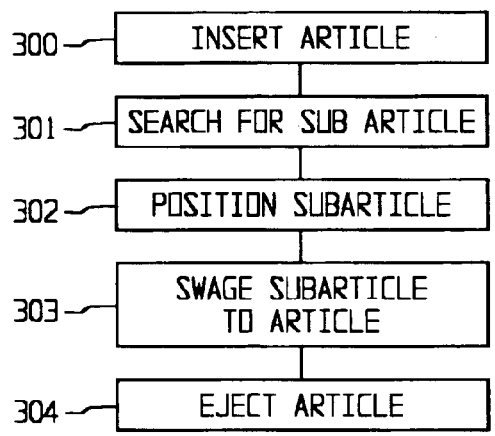
FIG. 23 is a flow chart illustrating one embodiment of the method of swaging one article to another article, of the present invention.

Referring to FIG. 23, the method of swaging a subarticle (for example one or more marker bands) to an article (for example a catheter) comprises the step 300 of inserting an article with a subarticle propositioned (but not swaged) thereon. The subarticle is preferably located in a general swaging region, but may be simply placed thereon. The next step 301, involves searching for the subarticle. This involves searching for the beginning or some other predetermined point on the article and then searching for the subarticle as a function of this article location, and is preferably accomplished by actuating a conveyance mechanism such as the input handling system and advancing the article to one or more sensors thereof to sense the article point and then advancing a predetermined distance therefrom to arrive at the subarticle. Next, the subarticle is preferably position adjusted 302 by advancing the article a predetermined distance while the subarticle remains still. This is preferably accomplished by actuating the input handling system to move the located subarticle on the article into alignment with the swaging head, engaging the subarticle with a predetermined grasping force applied by actuating the stationary swaging head and advancing the article with the input handling system a predetermined distance while holding the subarticle in position. This properly orients the subarticle with respect to the article. Next the subarticle is swaged 303 to the article. This is preferably accomplished by maintaining the position of the input handling system, rotating the swaging head a predetermined number of degrees, and simultaneously pulse actuating the swaging head with a predetermined swaging force. Next the article is ejected 304 preferably by the input handling and output handling systems.

Figure 24:
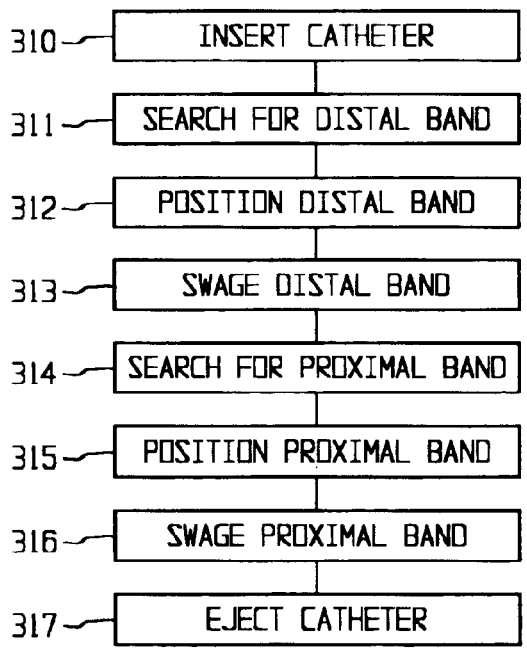
FIG. 24 is a flow chart illustrating another embodiment of the method of the invention for swaging marker bands to a catheter.

Referring to FIG. 24, the method of swaging two or more marker bands to a catheter comprises the step 310 of inserting an catheter with two bands propositioned (but not swaged) thereon. The bands are preferably located in general swaging regions. The next step 311, involves searching for the first or distal band. This involves searching for the beginning or some other predetermined point on the catheter and then searching for the distal band as a function of this catheter tip location, and is preferably accomplished by actuating a conveyance mechanism such as the input handling system and advancing the catheter to one or more sensors thereof to sense the catheter point and then advancing a predetermined distance therefrom to arrive at the band. Next, the distal band is preferably position adjusted 312 by advancing the catheter a predetermined distance while the band remains still. This is preferably accomplished by actuating the input handling system to move the located band on the catheter into alignment with the swaging head, engaging the band with a predetermined grasping force applied by actuating the stationary swaging head and advancing the catheter with the input handling system a predetermined distance while holding the band in position. This properly orients the band with respect to the catheter. This band searching and positioning step can be repeated one or more times to find and position further bands. Next the distal band is swaged 313 to the catheter. This is preferably accomplished by maintaining the position of the input handling system., rotating the swaging head a predetermined number of degrees, and simultaneously pulse actuating the swaging head with a predetermined swaging force. The next step 314, involves searching for the second or proximal band. This involves searching for the proximal band as a function of this distal swaging location, and is preferably accomplished by actuating a conveyance mechanism such as the input handling system and advancing the catheter a predetermined distance therefrom to arrive at the proximal band. Next, the proximal band is preferably position adjusted 315 by advancing the catheter a predetermined distance while the proximal band remains still. This is preferably accomplished by actuating the input handling system to move the located proximal band on the catheter into alignment with the swaging head, engaging the proximal band with a predetermined grasping force applied by actuating the stationary swaging head and advancing the catheter with the input handling system a predetermined distance while holding the band in position. This properly orients the band with respect to the catheter. This band searching and positioning step can be repeated for further bands. Next the proximal band is swaged 316 to the catheter. This is preferably accomplished by maintaining the position of the input handling system, rotating the swaging head a predetermined number of degrees, and simultaneously pulse actuating the swaging head with a predetermined swaging force. Next the catheter is ejected 317 preferably by the input handling and output handling systems.

Figure 20:
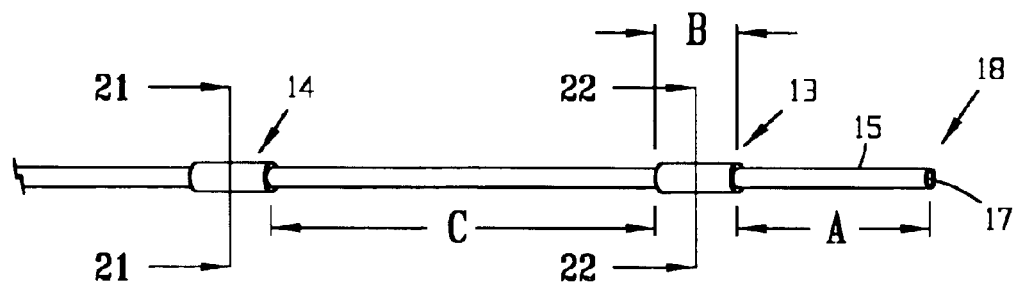
FIG. 20 is a perspective view of a portion of the catheter of FIG. 19.
Figure 21:
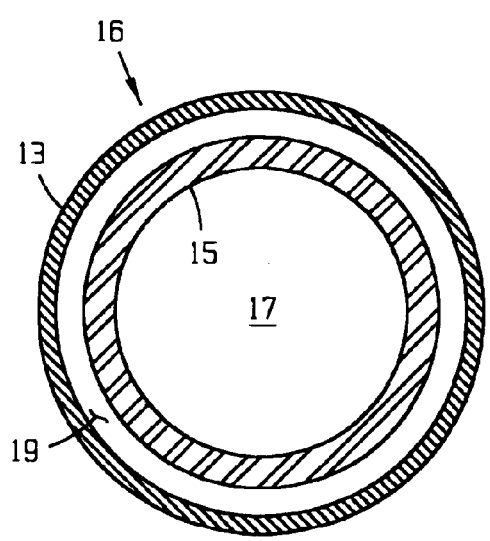
FIG. 21 is a crossectional view of the catheter taken along line 21—21 of FIG. 20.
Figure 22:
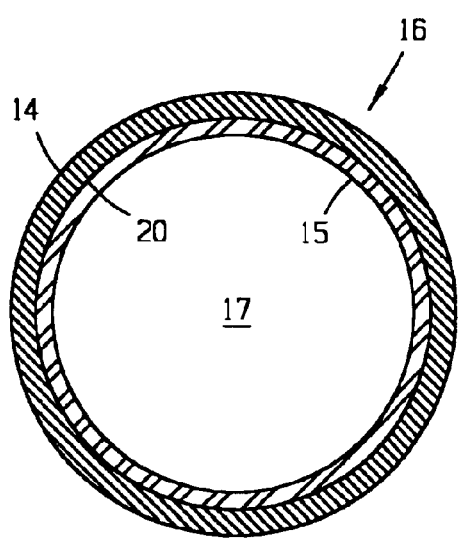
FIG. 22 is a crossectional view of the catheter taken along line 22—22 of FIG. 20.
Figure 25:
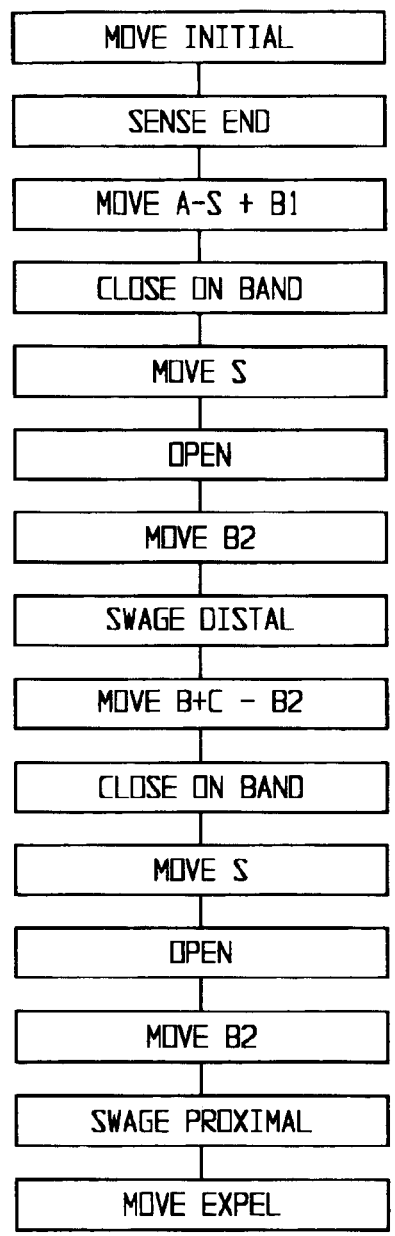
FIG. 25 is a flow chart illustrating a particular embodiment of the method of swaging marker bands on the catheter shown in FIG. 20.///

Referring to FIG. 25, a further preferred method of swaging a pair of marker bands to the catheter shown in FIG. 20 is illustrated wherein "A" is the distance from the tip to the distal band. "B" is the length of a band, and "C" is the distance from the distal band to the proximal band, and "S" is the slide distance that the band can be preset from the ending or final position. S cannot be larger than the C position and must take into account the die width. Further, A−S+1=Distal Band Placement and A+B+C−S+1=Proximal Band Placement.

Although the system, apparatus and method has been described in connection with the field of medical devices, and in particular, marker bands, it can readily be appreciated that it is not limited solely to such field, and can be used in other fields including, but not limited to aviation, electronics, industrial processes, computers, telecommunications ammunition, and the like.

The descriptions above and the accompanying drawings should be interpreted in the illustrative and not the limited sense. While the invention has been disclosed in connection with an embodiment or embodiments thereof it should be understood by those skilled in the art that there may be other embodiments which fall within the scope of the invention as defined by the claims. Where a claim, if any, is expressed as a means or step for performing a specified function it is intended that such claim be construed to cover the corresponding structure, material, or acts described in the specification and equivalents thereof including both structural equivalents and equivalent structures, material-based equivalents and equivalent materials, and act-based equivalents and equivalent acts.

What is claimed is:

1. A swager comprising an article input mechanism, a radial compression swaging head with a central swaging aperture aligned with the input mechanism to receive an input article from the article input mechanism and to swage the article, and an output mechanism aligned with the swaging head to receive the swaged article, wherein the article input mechanism has a first input roller assembly for receiving and conveying an article, a first sensor for detecting a predetermined aspect of the article, a second input roller assembly for receiving and conveying the article, a positioning roller assembly for precisely aligning the article with respect to the swaging head, and a second sensor all constructed and arranged in a streamwise orientation.

2. The swager of claim 1, wherein the article input mechanism has at least one conveyance mechanism to convey the article.

3. The swager of claim 2, wherein the at least one conveyance mechanism has at least one rotatable roller.

4. The swager of claim 1, wherein the article input mechanism has at least one sensor for detecting a predetermined aspect of the article.

5. The swager of claim 1, wherein the swaging head includes a die plate and an closing plate pivotally coupled with respect to each other.

6. The swager of claim 1, wherein the swaging head comprises a unitary die plate including a plurality of die segments movably coupled to each other to provide a radial compressive force to the article disposed in the central swaging aperture.

7. The swager of claim 6, wherein swaging head is rotatable.

8. The swager of claim 1, adapted for swaging at least one marker band to a medical catheter.

9. A swager for swaging marker bands to a medical catheter, comprising:
   a. an article input mechanism, the article input mechanism having a first input roller assembly for receiving and conveying an article, a first sensor for detecting a predetermined aspect of the article, a second input roller assembly for receiving and conveying the article, a positioning roller assembly for precisely aligning the article with respect to the swaging head, and a second sensor all constructed and arranged in a streamwise orientation;
   b. a radial compression swaging head with a central swaging aperture, the swaging head being aligned and communicatively coupled with the input mechanism to receive an input article from the article input mechanism and to swage the article, the swaging head being rotatable and including:
      i. a unitary die plate including a plurality of die segments movably coupled to each other to provide a radial compressive force to the article disposed in the central swaging aperture; and
      ii. closing plate pivotally coupled with respect to each other; and
   c. an output mechanism aligned and communicatively coupled with the swaging head to receive the swaged article.

10. A swaging apparatus comprising a unitary plate including a plurality of segments movably coupled to each other and defining a central swaging aperture, the segments being constructed and arranged to provide radial compressive force to an article disposed in the central swaging aperture, further comprising a circumferential base, the segments being centrally arranged with respect to the base and connected thereto, and wherein each segment is connected to the base by a radial flexure constructed as a beam and having a central beam axis aligned with the central swaging aperture.

11. The swaging apparatus of claim 10 wherein there are at least three segments.

12. The swaging apparatus of claim 11, wherein there are five segments.

13. The swaging apparatus of claim 10, wherein each segment has a circumferential flexure constructed of a beam extending from a neighboring segment, the circumferential flexure being constructed and arranged to couple movement with two neighboring segments.

14. The swaging apparatus of claim 10, wherein each segment has a pivot point, whereby application of a force on the segment causes the segment to pivot about the pivot point and apply a radial compressive force to article disposed in the central swaging aperture.

15. The swaging apparatus of claim 14, wherein the apparatus further comprises a closing plate pivotally coupled via the pivot points, and wherein the apparatus is rotatable.

16. The swaging apparatus of claim 10, adapted for swaging at least one at least one marker band to a medical catheter.

17. A swaging apparatus for swaging a marker band to a medical catheter, comprising:
   a. a unitary die plate including:
      1. at least three die segments movably coupled to each other and defining a central swaging aperture, the segments being constructed and arranged to provide radial compressive force to an article disposed in the central swaging aperture, the die plate further comprising
      2. a circumferential base, the segments being centrally arranged with respect to the base and connected thereto, wherein each segment:
         i. is connected to the base by a radial flexure constructed as a beam and having a central beam axis aligned with the central swaging aperture;
         ii. has a circumferential flexure constructed of a beam extending from a neighboring segment, the circumferential flexure being constructed and arranged to couple movement with two neighboring segments, and
         iii. has a pivot point, whereby application of a force on the segment causes the segment to pivot about the pivot point and apply a radial compressive force to article disposed in the central swaging aperture; and
   b. a closing plate pivotally coupled via the pivot points, and wherein the apparatus is rotatable.

* * * * *